Figure 1:
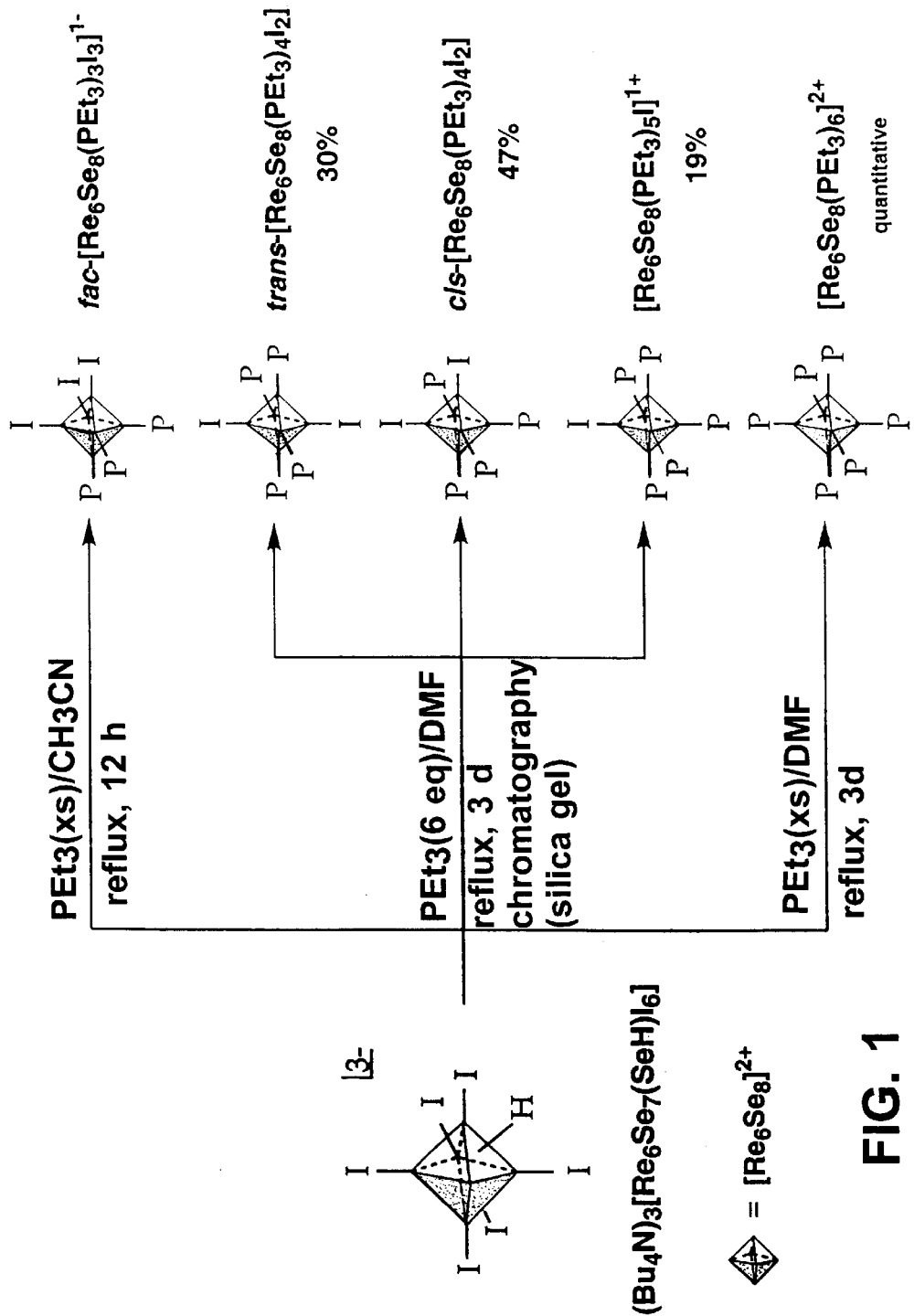

United States Patent [19]
Long et al.

[11] Patent Number: 5,804,161
[45] Date of Patent: Sep. 8, 1998

[54] CONTRAST AGENTS

[75] Inventors: Jeffrey R. Long; Xhiping Xheng; Richard H. Holm, all of Cambridge, Mass.; Shi-Bao Yu, Wayne, Pa.; Michael Droege, Livermore, Calif.; William A. Sanderson, Wayne, Pa.

[73] Assignee: Nycomed Salutar Inc., Wayne, Pa.

[21] Appl. No.: 704,009

[22] Filed: Aug. 26, 1996

Related U.S. Application Data

[63] Continuation of Ser. No. 649,000, May 14, 1996, abandoned.

[51] Int. Cl.$^6$ .............................. A61K 49/04; C07F 15/00
[52] U.S. Cl. ........................... 424/9.42; 514/492; 556/21; 556/23; 556/45; 556/136
[58] Field of Search ................................. 556/21, 23, 45, 556/136; 514/492; 424/9.42

[56] References Cited

FOREIGN PATENT DOCUMENTS

WO 91 14460 A 10/1991 WIPO.

OTHER PUBLICATIONS

Long et al., Angew, Chem. Int. Ed. Engl., vol. 34, No. 2, pp. 226–229, Feb. 3, 1995.

Mironov et al., Inorganic Chemistry, vol. 35, No. 10, pp. 2709–2710, May 8, 1996.

Chemical Abstracts, vol. 123, No. 18, 30 Oct. 1995; Columbus, Ohio, Abstract No. 245181w, Uriel, S. et al. "Solution Chemistry of Chalcohalide Hexanuclear Rhenium Cluster Monoanions: Substitution Reactions . . . ".

Journal Of The American Chemical Society, vol. 118, No. 19, 1996, pp. 4603–4616, Long, J.R. et al., "A Solid–State Route to Molecular Clusters: Access to the Solution Chemistry of . . . ".

Journal Of The American Chemical Society, vol. 119, No. 3, 1997, pp. 493–498, Mironov, Y.V. et al., "Cocrystallized Mixtures and Multiple Geometries: Syntheses, Structures and NMR Spectroscopy of . . . ".

Journal Of The American Chemical Society, vol. 119, No. 9, 1997, pp. 2163–2171, Zheng, Z. et al., "A Basis Set of Re6Se8 Cluster Building Blocks and Demonstration of their Linking Capability: . . . ".

Alain Penicaud et al., "Hydrogen–Bond Tuning of Macroscopic Transport Properties . . . ", J. Am. Chem. Soc. 1993, 115, 4101–4112.

Omar M. Yaghi et al., "Rhenium–Selenium–Chlorine Solid Phases: Cluster Excision and Core Substitution . . . ", Inorg. Chem. 1992, 31, 4778–4784.

*Primary Examiner*—Porfirio Nazario-Gonzalez
*Attorney, Agent, or Firm*—Fish & Richardson P.C.

[57] ABSTRACT

Compounds of formula (I)

$$[M_6Q_8B_nL_{6-n}]^x$$

where M is Re or Rh;
each Q is a bridging atom selected from O, S, Se and Te;
B is a monovalent non-bridging atom or moiety;
L is a PR$_3$ group in which R is C$_{1-6}$ alkyl or aryl, optionally substituted on the alkyl or aryl group by one or more water-solubilizing groups such as an amine or hydroxidy group, or the three R groups together form a C$_{6-10}$ trivalent group which may also contain up to three nitrogen or oxygen atoms;
n is an integer from 0 to 6;
and x is an integer from −2 to +4, representing the overall charge of the cluster, which when non-zero is accompanied by one or more counter ions of equal and balancing charge, and contrast media, particularly X-ray contrast media, containing them.

9 Claims, 7 Drawing Sheets

TERMINAL LIGAND SUBSTITUTION OF $[Re_6Se_8i_6]^{4-}$

= $[Re_6Se_6]^{2+}$ pale yellow
aqueous solution $Cs_4[Re_6Se_8I_6]$ →(TPA (xs)/$H_2O$, reflux, 12h) $[Re_6Se_8(TPA)_6]^{2+}$
quantitative $[Re_6Se_8(TPA)_6]^{2+}$

- quantitative
- pale yellow aqueous solution

TERMINAL LIGAND SUBSTITUTION OF $[Re_6Se_7(SeH)I_6]^{3-}$ BY MeCN $[Re_6Se_8(MeCN)_6]^{2+}$ $(Bu_4N)_3[Re_6Se_7(SeH)I_6]$ $\downarrow$ AgBF$_4$ (xs)
MeCN
25°C, 5 min $[Re_6Se_8(MeCN)_6]^{2+}$

- bare $[Re_6Se_8]^{2+}$ core solvated in MeCN
- universal starting material for ligand substitution
- pale yellow aqueous solution From [Re$_6$Se$_8$(MeCN)$_6$](BF$_4$)$_2$·4MeCN (orange-red elongated rhombohedral crystals)

CONTRAST AGENTS

CROSS REFERENCE TO RELATED APPLICATION

This application is a continuation of Ser. No. 08/649,000, Filed May 14, 1996, now abandoned.

The present invention relates to novel multinuclear clusters, their preparation and use in diagnostic imaging, in particular X-ray imaging, and to contrast media containing such moieties.

All diagnostic imaging is based on the achievement of different signal levels from different structures within the body. Thus in X-ray imaging for example, for a given body structure to be visible in the image, the X-ray attenuation by that structure must differ from that of the surrounding tissues. The difference in signal between the body structure and its surroundings is frequently termed contrast and much effort has been devoted to means of enhancing contrast in diagnostic imaging since the greater the contrast between a body structure and its surroundings the higher the quality of the images and the greater their value to the physician performing the diagnosis. Moreover, the greater the contrast the smaller the body structures that may be visualized in the imaging procedure, i.e. increased contrast can lead to increased spatial resolution.

The diagnostic quality of images is strongly dependent on the inherent noise level in the imaging procedure—and the ratio of the contrast level to the noise level can thus be seen to represent an effective diagnostic quality factor for diagnostic images.

Achieving improvement in such a diagnostic quality factor has long been and still remains an important goal. In techniques such as X-ray and ultrasound, one approach to improving the diagnostic quality factor has been to introduce contrast enhancing materials, contrast agents, into the body region being imaged.

Thus in X-ray for example early examples of contrast agents were insoluble inorganic barium salts which enhanced X-ray attenuation in the body zones into which they distributed. More recently the field of X-ray contrast agents has been dominated by soluble iodine containing compounds such as those marketed by Nycomed AS under the trade names omnipaque and Amipaque.

Much recent work on X-ray contrast agents has concentrated on aminopolycarboxylic acid (APCA) chelates of heavy metal ions and, recognising that effective imaging of many body sites requires localization at the body sites in question of relatively high concentrations of the metal ions, there have been suggestions that polychelants, that is substances possessing more than one separate chelant moiety, might be used to achieve this.

More recently it has been found that contrast enhancement may be achieved particularly effectively by the use of multinuclear cluster complexes, that is complexes wherein the complexed moiety itself comprises two or more contrast enhancing atoms or for X-ray two or more heavy atoms. See WO91/14460 and WO92/17215.

For the sake of clarity, the word "atom" is used to refer to ionic and covalently bonded forms and not simply to isolated uncharged atoms. Moreover it will be understood that the complexed moiety, while it is polynuclear, is not so large as to be considered to be a particle itself. Thus it will generally have maximum dimensions of 80 Å or less, especially 40 Å or less.

Attention is now turning to the development of contrast agents which will be of use in a variety of areas, for example in ECF, blood pool and liver imaging, and which will possess desirable characteristics such as high quality of X-ray attenuation, high water solubility and stability, high stability in air, low charge thus giving acceptable osmolality and viscosity, and ease of manufacture by means of convenient syntheses with good yields.

The present invention relates to improvements in the types of prior art multinuclear moieties described above and provides compounds which can satisfy some or all of the desirable criteria just mentioned. Thus in a first aspect there are provided compounds of formula (I)

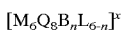

where M is Re or Rh;
each Q is a bridging atom selected from O, S, Se and Te;
B is a monovalent non-bridging atom or moiety, for example a nitrile or isonitrile such as MeCN or MeNC or an amide such as dimethyl formamide, preferably a halogen or pseudohalogen such as Cl, Br or SCN and particularly preferably I;
L is a $PR_3$ group in which R is $C_{1-6}$ alkyl or aryl, preferably a water soluble group, optionally substituted on the alkyl or aryl group by one or more water-solubilising groups such as an amine or hydroxidy group, or the three R groups together form a $C_{6-10}$ trivalent group which may also contain up to three nitrogen or oxygen atoms, for example forming with the phosphorus atom a triazaphospha-adamantane group;
n is an integer from 0 to 6, preferably from 0 to 3;
and x is an integer from −2 to +4, representing the overall charge of the cluster, which when non-zero is accompanied by one or more counter ions of equal and balancing charge, preferably a physiologically acceptable counterion.

The invention also encompasses dimers of the abovementioned compounds, for example the $[Re_{12}Se_{16}(PEt_3)_{10}]^{4+}$ dimer described in more detail hereinafter. Such dimers are expected to possess still greater X-ray absorption efficacy and/or reduced osmotoxicity.

Counter-ions which can balance any charge on the clusters include $Cl^-$, $Br^-$, $I^-$, $SCN^-$, acetate, citrate, $ClO_4^-$, triflate, $BF_4^-$, $PF_6^-$, $Na^+$, $K^+$, $Cs^+$, $Ca^{2+}$, $Mg^{2+}$, N-methyl glucosamine, meglumine, $R_4N^+$ where R is for example Et or Bu, and $Ph_4P^+$. Charge on the clusters can also be balanced by one or more chelating ligands as discussed in more detail hereinafter.

A further aspect of the invention provides a diagnostic imaging contrast medium comprising a compound of formula (I) complexed with one or more ligand molecules.

Viewed from a further aspect the invention provides compounds of formula (I) for use as diagnostic imaging contrast agents.

Viewed from a still further aspect the invention provides a diagnostic imaging contrast medium comprising a compound of formula (I) complexed with one or more ligand molecules, together with at least one sterile pharmaceutical carrier or excipient.

A yet further aspect of the invention provides a method of generating an image of a human or non-human animal, preferably mammalian, body which method comprises administering to said body a physiologically tolerable contrast enhancing amount of a compound of formula (I) complexed with one or more ligand molecules, and generating an image, preferably an X-ray image, of at least said part of said body.

The metal/iodine compounds of formula (I) are particularly advantageous in contrast media since they contain two excellent X-ray attenuators, a heavy metal and iodine. Thus contrast media based on these complexes are unique in providing the radiologist with a choice of the X-ray energies which may be used thus optimising the radiological procedure.

The metal/phosphine compounds of formula (I) are also particularly advantageous in that they are conveniently water-soluble, stable in water and also in the presence of oxygen, and in that they possess only a faint colour, typically yellow. Known intensely coloured multinuclear cluster contrast media can give rise to problems on administration to a subject undergoing imaging, in that they may cause discolouration of some or all of the subject's skin, and this discolouration may last for up to several days depending on the speed at which the contrast agent is excreted.

With regard to complexation of the compounds of the invention with ligand molecules and their subsequent formulation as contrast media, it is particularly convenient for the compounds of formula (I) to be presented as complexes containing EDTA, DTPA or other APCAs in place of the smaller ligands L. Such complexes are remarkably stable with regard to release of the heavy metal ions or clusters. APCAs may also serve as bridges between two or even more multinuclear clusters according to the invention thus providing oligomeric contrast agents.

It is particularly preferred that the electrical charge carried by the complexing moieties should substantially if not completely balance that carried by the complexed entity; for APCA chelants this may easily be achieved for example by omission, replacement or deactivation (e.g. by ester or amide formation) of one or more of the carboxyl moieties. Such "balanced" complexes would be expected to have low viscosity and acceptable osmolality due to their non-ionic form.

Many other suitable chelants are widely known or have been described in the literature, especially literature relating to heavy metal detoxification agents bifunctional chelants and chelate-based contrast agents, e.g. those described in WO-A-89/00557 (Berg) and the documents mentioned therein and in the search report appended thereto, U.S. Pat. No. 4,647,447 (Gries), U.S. Pat. No. 4,826,673 (Dean), EP-A-230893 (Felder), EP-A-217577 (Frincke), U.S. Pat. No. 4,652,519 (Warshawsky), U.S. Pat. No. 4,687,659 (Quay), and numerous other recent patent publications of Nycomed AS, Salutar Inc, Schering AG, Squibb, Bracco, Mallinckrodt, Dow and Guerbet.

The chelants useful for complexing the multinuclear moeity can be selected from a wide range of structures. Many of the most useful chelants are of general formula (II)

$$Z'(X(CHR_1)_a)_b XZ'$$

(where a is an integer of from 2 to 12, preferably 2 to 10, e.g. 2, 3, or 4; b is an integer of from 1 to 8, preferably 2, 3 or 4;

each R, independently is hydrogen, a hydrophilic or linking group (e.g. a hydroxyalkyl group) or two groups $R_1$, or one $R_1$ and one group Z', together represent a saturated or unsaturated heterocyclic or carbocyclic ring, preferably with 5–7 ring atoms;

each X independently is O, S, NZ' or PZ', each Z' indpendently is hydrogen, hydroxyalkyl, mercaptoalkyl, carboxyalkyl (or an amide or ester derivative thereof e.g. —$CH_2CONHCH_3$) or optionally hydroxy or mercapto substituted acyl, or is a side chain $((CHR_1)_a X^*)_c Z^*$ (where c is 1 to 4 and $X^*$ and $Z^*$ are as defined for X and Z' but do not represent any group containing a $X^*$ or $Z^*$ group) or two groups Z' together form a briding group $((CHR_1)_a X^*)_c (CHR_1)_a)$ or are salts thereof.

While polyamines, especially linear or cyclic polyamines, such as ethylenediamine,1,4,7-triazacyclononane and cyclen, can be used as chelants, in general APCAs are preferred, particularly DTPA, EDTA and derivatives thereof and other cyclic and non-cyclic APCAs as defined in WO-A-89/00557 and APCAs of formula III.

$$\begin{array}{c} (CHR_1)_d Y \quad (CHR_1)_d Y \\ | \qquad\qquad | \\ X(CHR_1)_e N\text{———}E\text{———}N(CHR_1)_e X \end{array}$$

where each $R_1$ is independently hydrogen or an optionally hydroxylated and/or alkoxylated alkyl group or an organic side chain adapted for the attachment of or attached to a macromolecule;

d and e each is an integer having a value of 1, 2 or 3;

each X is independently a group COOH or a derivative thereof;

each Y is independently a group X, $SR_1$, $OR_1$ or $N(R_3)_2$;

E is a group $(CHR_2)_f(X''(CHR_2)_f)_g$ where f is an integer of from 2 to 5, preferably 2 or 3, g is zero, 1 or 2, preferably zero or 1, each f preferably being 2 when g is non-zero, X'' is O, S or $N(CHR_1)_d Y$, preferably O or S, each $R_2$ is independently $R_1$ or, when the carbon to which it is attached is not bonded to a nitrogen, hydroxyl, or two $R_2$ groups, especially where f is 2, may together with the intervening carbons form a cycloalkyl group optionally substituted by hydroxyl or $R_1$ groups, and each $R_3$ is independently a group $R_1$ or $N(R_3)_2$ represents a preferably saturated heterocyclic group preferably having 5 or 6 ring members, optionally containing as a further heteroatom a nitrogen or oxygen and optionally substituted by $R_1$ groups.

In the chelants of formula XIII or XIV, any alkyl moiety preferably has a carbon atom content of up to 8, any cycloalkyl group preferably is a $C_{3-8}$, especially $C_{5-7}$, ring and any carboxyl derivative is preferably a $CON(R_3)_2$ or $CON(OH)R_1$ group.

Examples of suitable chelants include compounds of formulae:

$(HOOCCH_2)_2 NCH_2 CH_2 N(CH_2 COOH)_2$     (i)

$(HSCH_2CH_2)_2 NCH_2 CH_2 N(CH_2 CH_2 SH)_2$     (ii)

$H_2 NCH_2 CH_2 N(CH_2 COOH)CH_2 CH_2 N(CH_2 COOH)CH_2 CH_2 NH_2$     (iii)

$H_2 NCH_2 CH_2 N(CH_2 CH_2 SH)CH_2 CH_2 N(CH_2 CH_2 SH)CH_2 CH_2 NH_2$     (iv)

$HOOCCH_2(NCH_2 CH_2)_3 NCH_2 COOH$     (v)

$HSCH_2 CH_2(NCH_2 CH_2)_4 SH$     (vi)

$$\begin{array}{c}(CH_3)_2 CSH \qquad\qquad\qquad CSH(CH_3)_2 \\ | \qquad\qquad\qquad\qquad\qquad | \\ CH_2CO-N-(CH_2)_y-N-CO-CH_2 \\ | \qquad\qquad | \\ (CH_2)_y \qquad (CH_2)_y \\ | \qquad\qquad | \\ CH_2CO-N\bigg[(CH_2)_y-\ N-CO-CH_2 \\ | \qquad\qquad\qquad\qquad\qquad | \\ (CH_3)_2 CSH \qquad\qquad\qquad CSH(CH_3)_2\bigg]_z\end{array}$$ (vii)

(where y=6,7,8,9 or 10 and z=0 or 1)

$(HOOCCH_2)_2 NH$     (viii)

$(HSCH_2 CH_2)_2 NH$     (ix)

(HOOCCH₂)₂NCH₂CH₂N(CH₂COOH)CH₂CH₂N(CH₂COOH)
    CH₂CH₂N(CH₂COOH)₂  (x)

(HSCH₂CH₂)₂NCH₂CH₂N(CH₂CH₂SH)CH₂CH₂N(CH₂CH₂
    SH)CH₂CH₂N(CH₂CH₂SH)₂  (xi)

(HOOCCH₂)₂N(CH₂CH₂NH)₂CH₂CH₂N(CH₂COOH)₂  (xii)

(HSCH₂CH₂)₂N(CH₂CH₂NH)₂CH₂CH₂N(CH₂CH₂SH)₂  (xiii)

pyridine-2,6-dicarboxylic acid  (xiv)

2,6-bis-mercaptomethyl-pyridine  (xv)

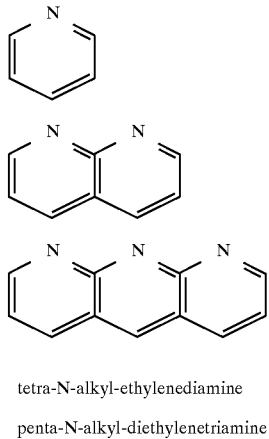

(xvi)

(xvii)

(xviii)

tetra-N-alkyl-ethylenediamine  (xix)

penta-N-alkyl-diethylenetriamine  (xx)

and the phosphorus analogues of these nitrogen-donor based ligands.

For the M₆Q₈ complexes of the invention chelants such as (xvi) are of particular interest. Chelants such as (ii), (vi), (xi) and (xiii) are also of particular interest since the clusters of the present invention prefer sulphur ligands.

polysaccharide or poly-sugar alcohol, e.g. dextran or starch. Such macromolecules are discussed extensively in the recent literature relating to contrast agents.

The chelants of formulae II and III are already known from the literature or may be prepared in analogous fashion to the known chelants. The preparation of chelants of formula II and III will however generally fall into one of two categories: derivatization of a polyamine or amination of polyfunctional compounds. Derivatization can be performed in one or more stages and the groups introduced may, in intermediate or final stages, be subject to reduction or deprotection steps.

The polyamine starting materials are either available commercially or may be prepared by routine methods. Thus for example commercially suitable polyamines include NH₂(CH₂)₂₋₅NH₂, NH₂(CH₂)₂O(CH₂)₂NH₂, NH₂CH₂CHOHCH₂NH₂, NH₂(CH)₂S(CH₂)₂NH₂. Optionally substituted polyamines may also be prepared by methods described in or analogous to those of EP-A-287465 (Schaeffer), WO-A-89/00557 (Berg), Brechbiel et al. Inorg. Chem. 25: 2772 (1986), Yeh et al. Analytical Biochem. 100: 152 (1979), Vögtle et al. Liebigs Ann. Chem. (1977) 1344, Kasina et al. J. Med. Chem. 29: 1933 (1986), Bedell et al. Inorg. Chem. 21:874 (1982), etc.

Derivatization of the polyamines may be effected using alkylation agents such as those described by EP-A-230893 (Felder), e.g. HalCH₂COL", HalCH(COOH)CH₂O Benzyl, or HalCH(COOH)₂ (where Hal is Cl or Br and L"is OH, NHAlkyl or NAlkyl₂ (e.g NHCH₃ or N(CH₃)₂) or HalCH₂NAlkyl₂ (e.g. ClCH₂N(CH₃)₂), followed where necessary by deprotection of protected groups. Examples of such schemes include

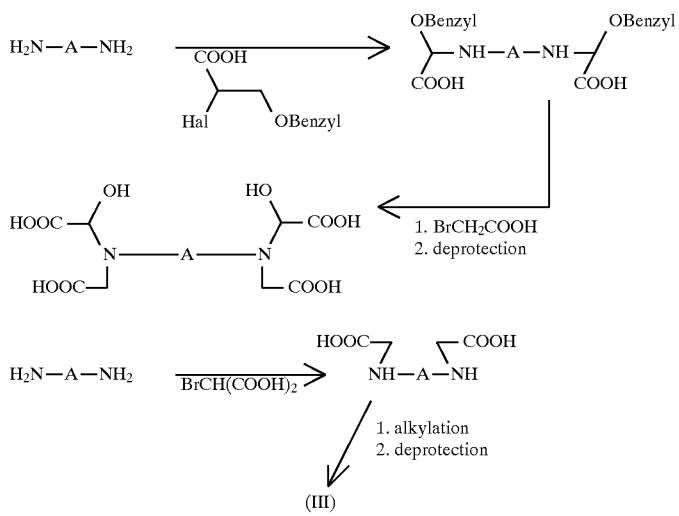

The use of macrocyclic chelants, e.g. those of formula (vii) is particularly preferred as a means by which to enhance solution stability. Particularly preferred chelants include cyclen, EDTA, EDTA-BMA, DTPA, DOTA, DO3A, HP-DO3A, the 6-oxa and 6-thia analogues of DTPA and amides thereof, e.g. DTPA-BMA and DTPA-BMO.

Where the chelant is to be attached to a macromolecule, this may conveniently be any tissue, organ or cell targeting macromolecule, for example a biomolecule such as a protein, an antibody or antibody fragment, or alternatively it may be a biologically relatively inert material such as a Selective alkylation of amines is described by Nordlander et al. Tetr. Lett. (1978) 4987 and J. Org. Chem. 49: 133 (1984) and by Aspinall et al. JACS 63: 852 (1941). Many other appropriate derivatization procedures are described in the literature.

For the reductive procedure discussed above, reaction may be of many of the same or similar polyamines with aldehyde, carboxyl or carboxyl derivative compounds followed by reduction of the amide carbonyl groups, e.g. using sodium cyanoborohydride or diborane, e.g. as in the scheme

CH₂SO₂COOCH₃ + NH₂—A—NH₂

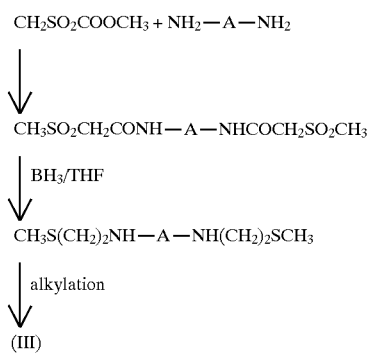

(III)

The resulting thioesters could equally be produced by reaction of an aminocarboxylic acid reagent with a chloroalkylsulphide, e.g.

HOOCCH₂NH—A—NHCH₂COOH

| CH₃S(CH₂)₂Cl
↓

CH₃SCH₂CH₂(HOOCCH₂)N—A—N(CH₂COOH)CH₂CH₂SCH₃

As mentioned above, the chelants of formula (XIV) can also be produced by amination of polyfunctional reagents. One example of this procedure is given by Huber et al. J. Chem. Soc. Chem. Comm. (1989) 879, i.e.

BrCH₂CH₂Br + NH₂CH₂CH₂N(CH₃)₂
↓

(CH₃)₂N(CH₂)₂ NH(CH₂)₂NH(CH₂)₂N(CH₃)₂

The resulting polyamine can then be converted to a compound of formula XIV by reaction with HOCH₂CN followed by hydrolysis. A wide variety of other polyhalo and amine compounds suitable for use in such reactions are available commercially or may be prepared using text book methods.

In a similar manner, polyfunctional acids may be reacted with appropriate amines if necessary after activation of the acid groups, reduction of the amide and alkylation will yield chelants of formula XIV. Commercially available polyfunctional acids utilizable in this way include for example

HOOCBCOOH where B is —CHOHCH₂CH₂—, —(CHOH)₂—, —(CH₂)₁₋₃— or

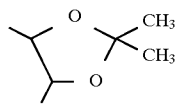

In order to attach the chelant to a macromolecule, e.g. a protein or a carbohydrate, the chelant may be provided with a reactive side chain (e.g. described by Meares et al. Anal. Biochem. 142: 68(1984), etc). Alternatively attachment can be efected for example using the methods developed by Salutar Inc. (See for example WO-A-90/12050 and Sieving et al., Bioconjugate Chem. 1: 65–71 (1990)) or the mixed anhydride or cyclic anhydride methods of Krejcarek et al Biochemical and Biophysical Research Comm. 77: 881 (1977) or Hnatowich et al. Science 220: 613 (1983) etc. Attachment of the chelant may be either directly to the macromolecule or, preferably, to a an intermediate polymer, e.g. poly-L-lysine or polyethylene-imine, onto which a plurality of chelants may be loaded, e.g. as discussed in EP-A-331616 (Deutsch).

Thus for example the following macromolecule-linkable chelants are suggested in the literature:

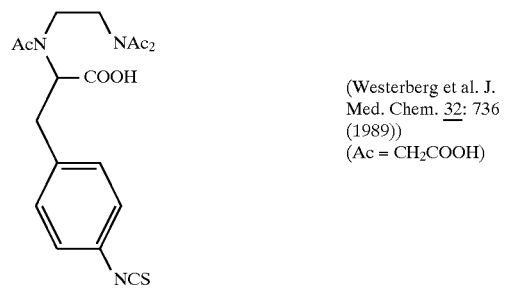

(Westerberg et al. J. Med. Chem. 32: 736 (1989))
(Ac = CH₂COOH)

(JACS 59: S + D 10 (1982))

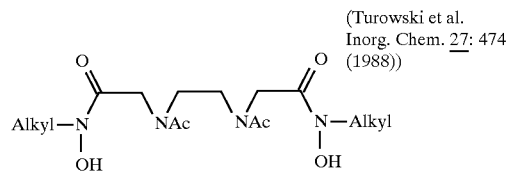

(Turowski et al. Inorg. Chem. 27: 474 (1988))

(Hernandez et al. An. Quim. Ser. B. 83: 172 (1987))

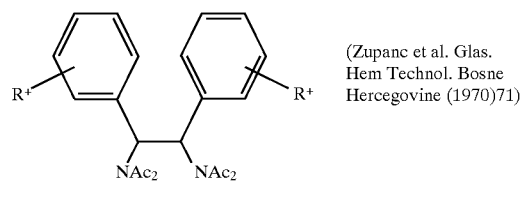

(R⁺ = NO₂, OH)

(Zupanc et al. Glas. Hem Technol. Bosne Hercegovine (1970)71)

(EP-A-217577 (Frinke))

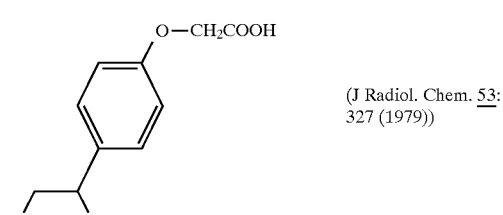

(J Radiol. Chem. 53: 327 (1979))

-continued

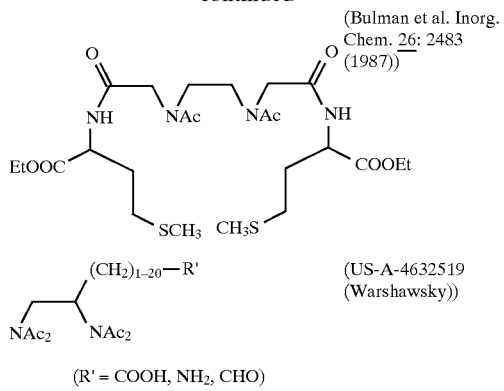
(Bulman et al. Inorg. Chem. 26: 2483 (1987))

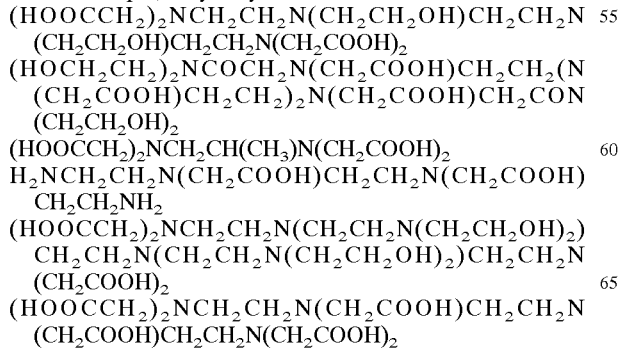
(US-A-4632519 (Warshawsky))

(R' = COOH, NH$_2$, CHO)

The bidentate thiolates and oxalates and the tridentate tris-thiols of Holm et al. (see JACS 112: 8015–8023 (1990) and JACS 110: 2484–2494 (1988)) also may be used.

Interlinking of multinuclear clusters by the ligand(s) can be used to create oligomeric, for example dimeric, contrast media. The ligands may conveniently represent linear, branched or cyclic polyamino, polyaminocarboxylic or polycarboxylic acids. More specifically, they may be represented by the formula (IV):

$$(R^2)_2N[(CHR^4)_mNR^1]_n(CHR^4)_mN(R^2)_2 \quad (IV)$$

where each $R^1$ which may be the same or different and represents a group $R^2$ or a $C_{1-4}$alkyl, phen-$C_{1-4}$alkyl, $C_{1-4}$hydroxyalkyl or amino-$C_{1-4}$alkyl group or two $R^1$ groups may together represent a group $CH_2CH_2NR^3CH_2CH_2$ where $R^3$ is an $R^2$ group or a $C_{1-4}$ alkyl group optionally substituted by hydroxyl, carboxyl, aryl or amino groups;

n is 0, 1 or 2; each m is 2, 3 or 4 preferably 2; and each $R^4$ denotes a group $R^1$ or a carboxyl, hydroxyl or $C_{1-4}$alkoxy group; and each $R^2$ independently represents a hydrogen atom or an optionally amidated or esterified carboxy —($C_{1-4}$ alkyl) group, wherein any amide nitrogen is substituted by group selected from hydrogen atoms and optionally hydroxylated $C_{1-4}$ alkyl groups; preferably such that an $R^4$ or $R^1$ group contains a quaternary amine group.

Particularly preferably the ligands are represented by the formula V, VI or VII $$(R^2)_2NCH_2CH_2NR^1CH_2CH_2NR^1CH_2CH_2N(R^2)_2 \quad (V)$$

$$(R^2)_2NCH_2CH_2NCH_2CH_2N(R^2)_2 \quad (VI)$$
$$|$$
$$R^1$$

$$(R^2)_2NCH_2CHR^4N(R^2)_2 \quad (VII)$$

in which $R^1$, $R^2$ and $R^4$ are as defined above.

For example, they may be selected from (HOOCCH$_2$)$_2$NCH$_2$CH$_2$N(CH$_2$CH$_2$OH)CH$_2$CH$_2$N (CH$_2$CH$_2$OH)CH$_2$CH$_2$N(CH$_2$COOH)$_2$
(HOCH$_2$CH$_2$)$_2$NCOCH$_2$N(CH$_2$COOH)CH$_2$CH$_2$(N (CH$_2$COOH)CH$_2$CH$_2$)$_2$N(CH$_2$COOH)CH$_2$CON (CH$_2$CH$_2$OH)$_2$
(HOOCCH$_2$)$_2$NCH$_2$CH(CH$_3$)N(CH$_2$COOH)$_2$
H$_2$NCH$_2$CH$_2$N(CH$_2$COOH)CH$_2$CH$_2$N(CH$_2$COOH) CH$_2$CH$_2$NH$_2$
(HOOCCH$_2$)$_2$NCH$_2$CH$_2$N(CH$_2$CH$_2$N(CH$_2$CH$_2$OH)$_2$) CH$_2$CH$_2$N(CH$_2$CH$_2$N(CH$_2$CH$_2$OH)$_2$)CH$_2$CH$_2$N (CH$_2$COOH)$_2$
(HOOCCH$_2$)$_2$NCH$_2$CH$_2$N(CH$_2$COOH)CH$_2$CH$_2$N (CH$_2$COOH)CH$_2$CH$_2$N(CH$_2$COOH)$_2$ and

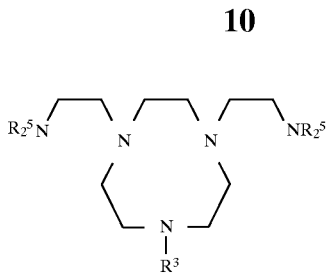

where each $R^5$ is hydrogen or carboxymethyl and $R^3$ is hydroxyalkyl or N-carboxymethylated amino alkyl.

Particularly preferably, they may be selected from (HOOCCH$_2$)$_2$NCH$_2$CH$_2$N(CH(CH$_2$OH)$_2$)CH$_2$CH$_2$N (CH$_2$COOH)$_2$ and (HOOCCH$_2$)$_2$NCH$_2$CH$_2$N(C(CH$_2$OH)$_3$) CH$_2$CH$_2$N(CH$_2$COOH)$_2$.

Further suitable ligands are shown in Table 1 below, and diamide, diester and dialcohol derivatives of them are also useful where the lipophilicity, stability and/or charge compensation of the ligand requires adjustment:

| NAME | STRUCTURE |
|---|---|
| EDTA | 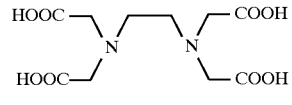 |
| Me-ETDA | 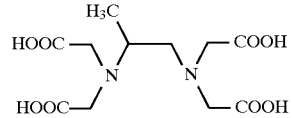 |
| EDPA | 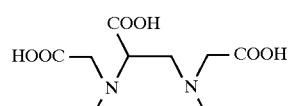 |
| PDTA | 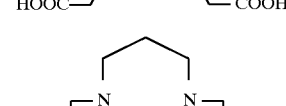 |
| HO-PDTA | 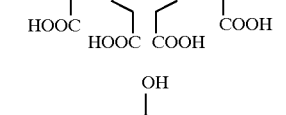 |
| MeO-PDTA | 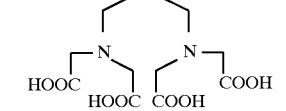 |
| CM-PDTA | 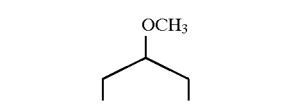 |

-continued

| NAME | STRUCTURE |
|---|---|
| BDTA | 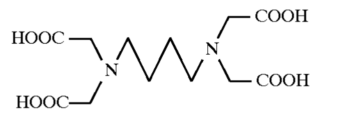 |
| OBETA | 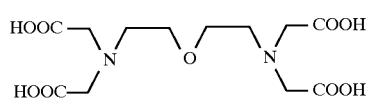 |
| Me-DTTA | 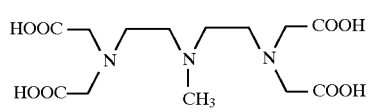 |
| Bz-DTTA | 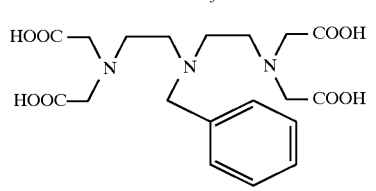 |
| HO-Et-DTTA | 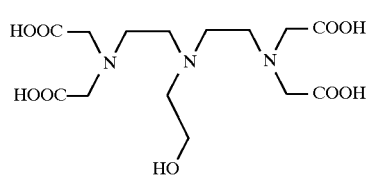 |
| serinol-DTTA | 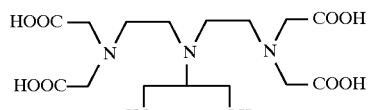 |
| DTPA | 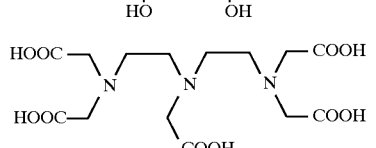 |
| EGTA | 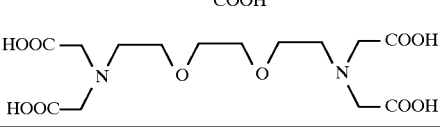 |

In the ligands described above, unless otherwise stated, any alkyl moiety preferably has a carbon atom content of up to 8, any cyclic group other than the macrocyclic skeleton of a macrocyclic ligand is preferably a three to eight membered ring and any carboxyl derivative is preferably an amide group.

In the complexes used in the invention, it is particularly preferred that the electrical charge carried by the ligands should substantially if not completely balance that carried by the clusters. Thus, for example, it is preferable to reduce the overall negative charge inherent in such a complex whilst simultaneously increasing the water solubility/hydrophilicity of the cluster complex.

We have found that this can be achieved by the use of so-called "charge compensation" chelate ligands which carry a positive charge, preferably in the form of a quaternary ammonium group located either in the backbone of the bridging ligand or, more preferably, in a backbone substituent of the ligand. On complexation with one or more clusters, such "charge compensation" ligands are capable of forming a zwitterionic complex with a lower overall ionic charge.

In addition, the positive centre of such "charge compensation" ligands may be functionalised with groups such as for example hydroxyl groups, which serve to increase the solubility/hydrophilicity of the resulting complex.

Two main approaches can be used to introduce charge compensation: (i) prepare positively charged ligands (such as quaternary ammonium containing) and then form a complex with the cluster; and (ii) start with a pre-formed cluster/ligand complex and use a chemical reaction at a non-tungsten coordinating functional group (amine, carboxylate, etc.) to introduce positive charge (quaternary ammonium for example).

The precise location of the positive centre on the chelate ligand has been found to affect the complexation reaction pathway and in some cases may shift the pathway away from formation of the desired complexes towards undesired polymeric materials.

Alternatively it is possible to introduce positive charge into a pre-formed complex. This approach uses a post-complexation functionalization of a pre-formed complex to derivatize a portion of the ligand in a complex that is not involved in coordinating to the metal. Charge compensation is achieved by either inducing a positive centre (such as alkylation to form a quaternary ammonium center at an amine of the ligand that is not involved in binding to tungsten) or by attaching a cationic functional group (such as a quaternary ammonium group) to a functional group of the ligand that is not attached to tungsten. This is an attractive approach because it overcomes any possible difficulties of complexation with positively charged ligands and because straightforward organic chemistry can be used to attach different types of hydrophilic and charged groups to already formed and purified complexes.

For adminstration to human or animal subjects, the chelated compounds of formulae (I) will conveniently be formulated together with pharmaceutical or veterinary carriers or excipient. The contrast media of the invention may conveniently contain pharmaceutical or veterinary formulation aids, for example stabilizers, antioxidants, osmolality adjusting agents, buffers, pH adjusting agents, colorants, flavours, viscosity adjusting agents and the like. They may be in forms suitable for parenteral or enteral administration, for example, injection or infusion or adminstration directly into a body cavity having an external voidance duct, for example the gastrointestinal tract, the bladder and the uterus. Thus the media of the invention may be in conventional pharmaceutical adminstration forms such as tablets, coated tablets, capsules, powders, solutions, suspensions, dispersions, syrups, suppositories etc; solutions, suspensions and dispersions in physiologically acceptable carrier media, e.g. water for injections, will however generally be preferred. Where the medium is formulated for parenteral administration, the carrier medium incorporating the multinuclear complex is preferably isotonic or somewhat hypertonic. Moreover, media for parenteral administration will preferably contain small quantities, e.g. 0.01 to 10 mole percent relative to the multinuclear complex of free chelants or of weak chelate complexes with physiologically tolerable chelated species (e.g. $Ca^{2+}$); small additions of sodium or calcium salts may also advantageously be made.

For use as X-ray contrast media, the media of the invention should generally have a heavy atom content of 1 millimole/l to 5 mole/l, preferably 0.1 to 2 mole/l. Dosages of from 0.5 to 1.5 mmoles/kg will generally be sufficient to provide adequate contrast although dosages of 0.8 to 1.2 mmoles/kg will normally be preferred.

For scintigraphy, dosages of the radioactive species will generally be lower.

Thus in summary the present invention provides a particularly effective means by which contrast media efficiency may be enhanced by increasing the relative proportion of molecular volume that is occupied by the contrast enhancing heavy metal atoms.

Figure 2:
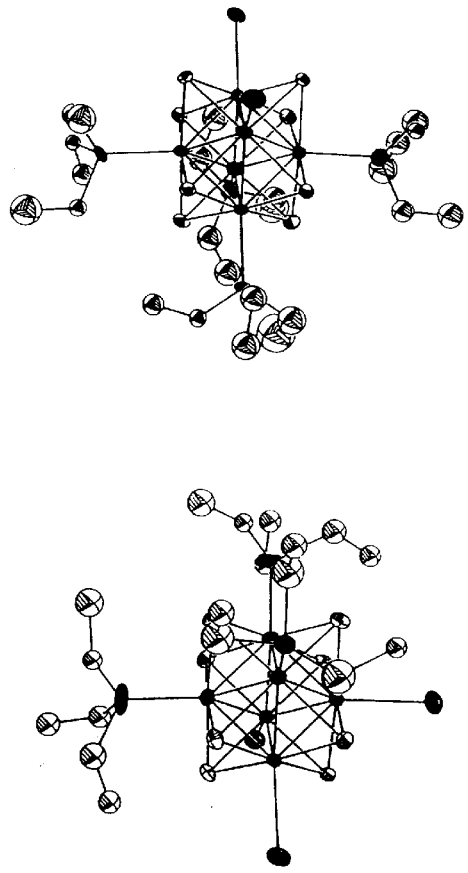
Figure 2:
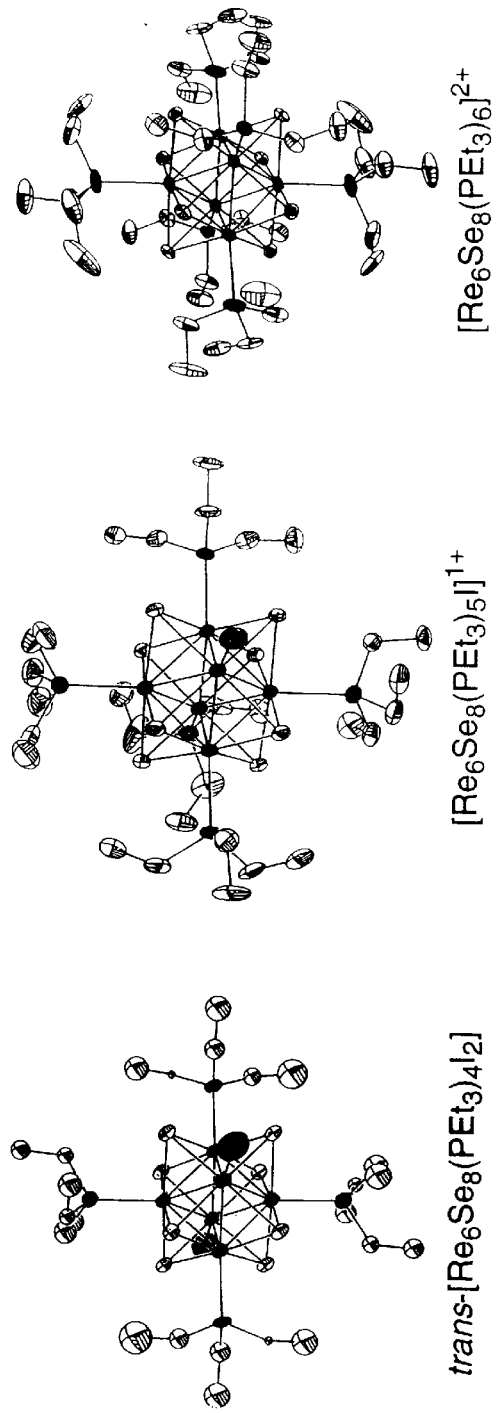
Figure 3:
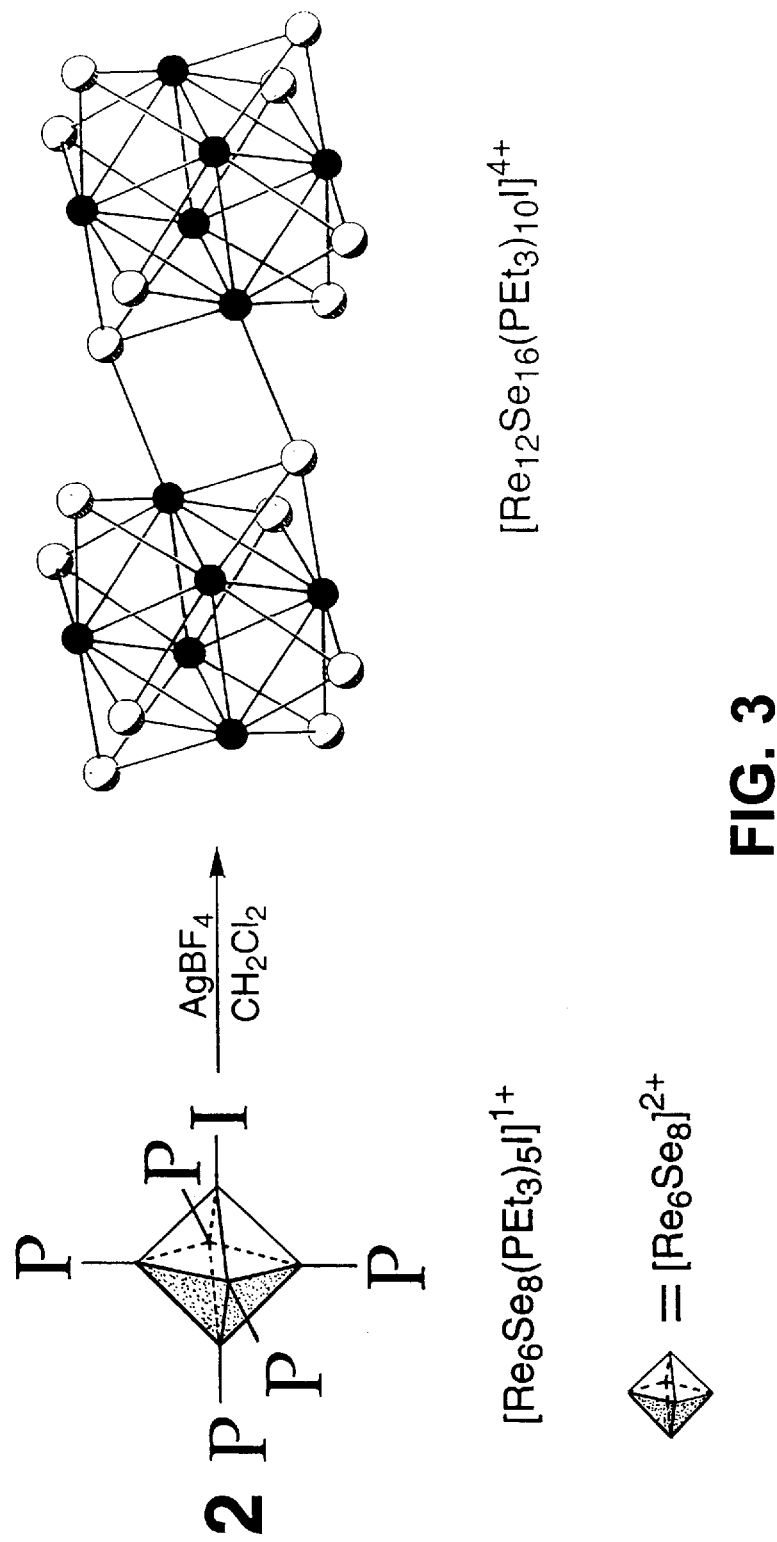
Figure 4A:
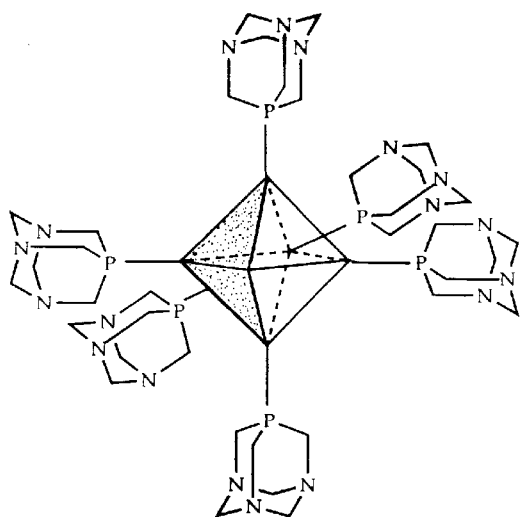
Figure 4A:
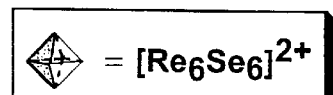
Figure 4A:
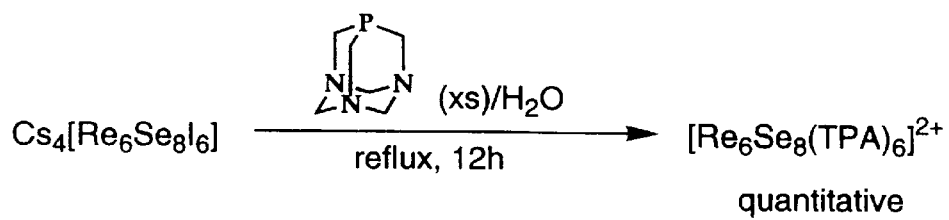
Figure 4B:
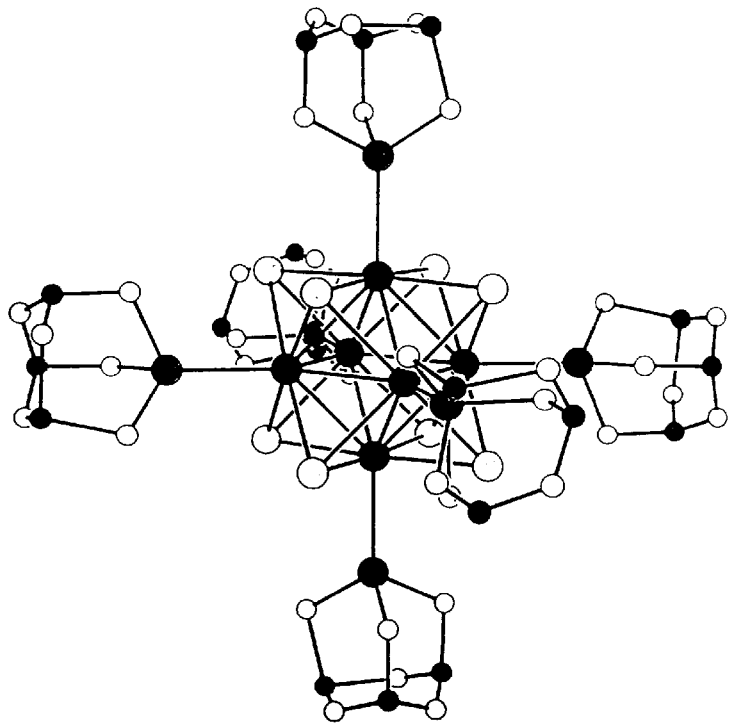
Figure 4B:
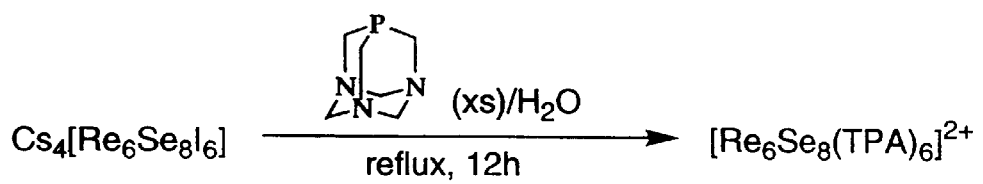
Figure 5A:
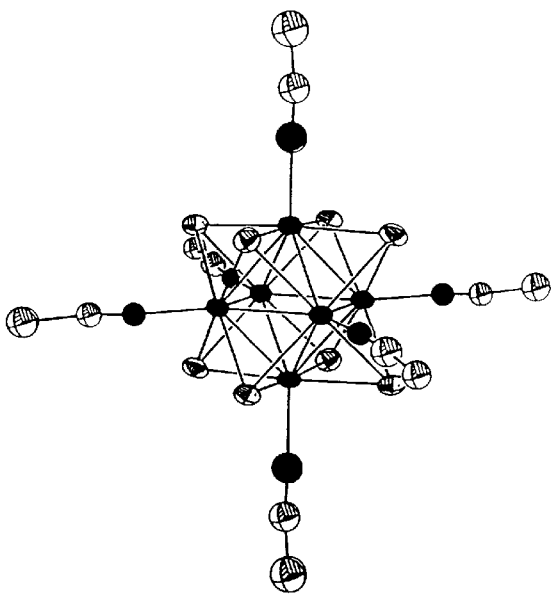
Figure 5B:
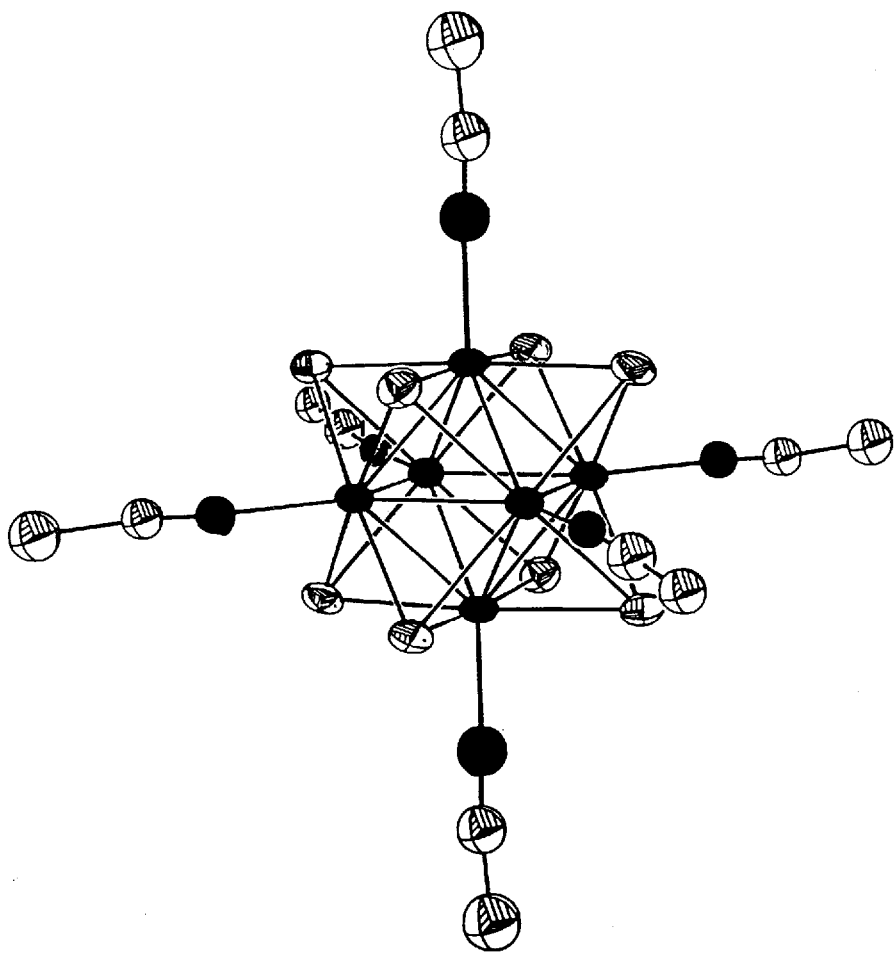

The present invention will now be illustrated further by the following non-limiting Examples with reference to the accompanying FIGS. 1–5 wherein:

FIG. 1 shows the terminal ligand substitution of $[Re_6Se_7(SeH)I_6]^{3-}$,

FIG. 2 shows the detailed structures of phosphine-substituted analogues of $(Bu_4N)_3[Re_6Se_7(SeH)I_6]$, FIG. 3 shows the detailed structure of $[Re_{12}Se_{16}(PEt_3)_{10}I]^{4+}$, FIG. 4a shows the terminal ligand substitution of $[Re_6Se_8I_6]^{4-}$, FIG. 4b shows the detailed structure of $[Re_6Se_8(1,3,5-triaza-7-phospha-adamantanyl)_6]^{2+}$, FIG. 5a shows the terminal ligand substitution of $[Re_6Se_7(SEH)I_6]^{3-}$, FIG. 5b shows the detailed structure of $[Re_6Se_8(MeCN)_6]^{2+}$.

EXAMPLE 1

Preparation of "n=6" Compounds $Cs_5Re_6S_8Br_7$

Liquid $Br_2$ (ca. 0.2 g) was added to a tared fused silica ampule; the ampule and its contents were accurately weighed and cooled with liquid nitrogen. A mixture of Re, S and CsBr (stoichiometric amounts bringing the total mass of reactants to ca. 4 g) was intimately ground and added to the ampule, which was then evacuated and sealed. The sample was heated (with reactants situated at the cooler end of the ampule) at 850° C. for 6000 min, cooled at 0.2° C./min to about 500° C., and air-quenched. The product crystallized as thick yellow-orange hexagonal plates.

EMPA:  $Cs_{5.15(6)}Re_{6.00(5)}S_{8.0(2)}Br_{7.5(2)}$.

$Cs_6Re_6S_8I_8$.

A fused silica ampule was charged with a ca. 2 g mixture of Re, S, $I_2$ and CsI in proportions corresponding to an overall stoichiometry of $Cs_8Re_6S_8I_{10}$ (two extra equivalents of CsI), and sealed under static vacuum. The sample was heated (with reactants situated at the cooler end of the ampule) at 850° C. for 6000 min, cooled at 0.2° C./min to about 500° C., and air-quenched. The product crystallized as thick yellow rectangular plates along with CsI and varying amounts of an insoluble black phase of unknown composition.

EMPA:  $CS_{6.17(5)}Re_{6.00(9)}S_{7.7(1)}I_{8.25(5)}$.

 $Cs_2Re_6Se_8Br_4$.

A 0.500 g mixture of Re, Se, ReBr$_5$ and CsBr in proportions corresponding to an overall stoichiometry of $Cs_5Re_6Se_8Br_7$ (three extra equivalents of CsBr) was intimately ground in a pure dinitrogen atmosphere, and sealed in a fused silica ampule under vacuum. The sample was heated (with reactants situated at the cooler end of the ampule) at 800° C. for 6000 min, cooled at 0.2° C./min to about 400° C., and air-quenched. The product crystallized (along with the excess CsBr) as metallic black needles.

$CsRe_6Se_8I_3$.

A fused silica ampule was charged with a stoichiometric 0.800 g mixture of Re, Se, $I_2$ and CsI, and sealed under vacuum. The sample was heated (with reactants situated at the cooler end of the ampule) at 850° C. for 6000 min, cooled at 0.2° C./min to about 400° C., and air-quenched. The product crystallized as metallic black elongated rhombic plates.

EMPA:  $Cs_{1.1(1)}Re_{6.0(1)}Se_{8.0(1)}I_{3.13(8)}$.

 $Cs_4Re_6Se_8I_6$.

A fused silica ampule was charged with a stoichiometric ca. 2 g mixture of Re, Se, $I_2$ and CsI, and sealed under static vacuum. The sample was heated (with reactants situated at the cooler end of the ampule) at 850° C. for 6000 min, cooled at 0.2° C./min to about 500° C., and air-quenched. The product crystallized as thick red rhombic plates. Occasional minor impurities of $CsRe_6Se_8I_3$ (insoluble) and CsI were also observed.

EMPA:  $CS_{4.5(2)}Re_{6.0(2)}Se_{7.6(9)}I_{6.4(2)}$.

 $(Bu_4N)_4[Re_6S_8Cl_6]$.

A 1.70 g portion of the product recovered from a reaction targeting $Cs_5Re_6S_8Cl_7$ was pulverized and stirred in 200 mL of 1M aqueous HCl for 45 min. The mixture was filtered to give a small amount of gray-black solid and a bright yellow filtrate. Solid KOH (26 g, 0.46 mol) was added to the filtrate and stirred until it completely dissolved. Excess $(Bu_4N)Cl$ (ca. 1 g) was added to the stirred solution which turned colorless upon formation of a yellow precipitate. The precipitate was collected by filtration and dissolved in 100 mL of acetonitrile to give a yellow-orange solution. The solution was reduced to dryness leaving a yellow-orange solid which was recrystallized by evaporation from a ca. 1:1 (v/v) mixture of acetone and toluene. The resulting yellow-orange plates were washed with successive 30 mL aliquots of toluene, water, toluene and pentane to afford 0.73 g (38%) of product. Absorption spectrum (MeCN): $\lambda_{max}$ ($\epsilon_M$) 377 (sh, 1860), 434 (1050), 537 (140) nm.

Anal. Calcd. for $C_{64}H_{144}Cl_6N_4S_8Re_6$: C, 30.07; H, 5.68; Cl, 8.32; N, 2.19; Re, 43.70; S, 10.03. Found: C, 29.88; H, 5.59; Cl, 10.11; N, 2.17; Re, 43.88; S, 10.11.

 $(Bu_4N)_3[Re_6S_7(SH)Cl_6]$.

The product recovered (1.96 g) from a reaction targeting $Cs_5Re_6S_8Cl_7$ was pulverized and stirred in 200 mL of 1M aqueous HCl for 30 min. The mixture was filtered to give a small amount of gray-black solid and a bright yellow filtrate. Excess $(Bu_4N)Cl$ (ca. 800 mg) was added to the stirred filtrate which turned colorless upon formation of a yellow precipitate. The precipitate was collected by filtration and dissolved in 100 mL of acetonitrile to give a yellow-orange solution. Several drops of water and ca. 0.5 mL of $SOCl_2$ were added to the stirred solution which underwent an immediate color change to red. The solution was reduced to dryness leaving a red solid which was recrystallized by evaporation from a ca. 1:1 (v/v) mixture of acetone and toluene. The resulting red plates were washed with successive 30 mL aliquots of toluene, water, toluene and pentane to afford 1.31 g (66%) of product. Absorption spectrum (MeCN): $\lambda_{max}$ ($\epsilon_M$) 378 (sh, 1820), 489 (785), 544 (1190) nm.

Anal. Calcd. for $C_{48}H_{109}Cl_6N_3S_8Re_6$: C, 24.91; H, 4.75; Cl, 9.19; N, 1.82; Re, 48.26; S, 11.08. Found: C, 24.83; H, 4.68; Cl, 9.24; N, 1.77; Re, 48.34; S, 11.21.

 $(Bu_4N)_4[Re_6S_8Br_6].H_2O$.

A 1.17 g portion of the product recovered from a reaction targeting $Cs_5Re_6S_8Br_7$ (as described above) was pulverized and stirred in 200 mL of 1M aqueous HBr for 30 min. The mixture was filtered to give a small amount of gray-black solid and a bright yellow filtrate. Solid NaOH (26 g, 0.65 mol) was added to the filtrate and the mixture was stirred until thge solid completely dissolved. Excess $(Bu_4N)Br$ (ca. 600 mg) was added to the stirred solution which turned colorless upon formation of a yellow precipitate. The precipitate was collected by filtration and dissolved in 100 mL MeCN to give a yellow-orange solution. The solution was reduced to dryness leaving a yellow-orange residue which was crystallized by evaporation from a ca. 1:1 (v/v) mixture of acetone and toluene. The resulting yellow-orange plates were washed with successive 30 mL aliquots of toluene, water, toluene and pentane to afford 0.73 g (58%) of pure product. Absorption spectrum (MeCN): $\lambda_{max}$ ($\epsilon_M$) 401 (sh, 1540), 443 (945), 545 (90) nm.

Anal. Calcd. for $C_{64}H_{146}Br_6N_4OS_8Re_6$: C, 27.06; H, 5.18; Br, 16.87; N, 1.97; Re, 39.32; S, 9.03. Found: C, 27.15; H, 5.16; Br, 16.76; N, 1.89; Re, 39.26; S, 9.18.

$(Bu_4N)_3[Re_6S_7(SH)Br_6]$.

The product recovered (3.48 g) from a reaction targeting $Cs_5Re_6S_8Br_7$ (as described above) was pulverized and stirred in 200 mL of 1M aqueous HBr for 30 min. The mixture was filtered to give a small amount of red-brown solid and a bright yellow filtrate. Excess $(Bu_4N)Br$ (ca. 1.5 g) was added to the stirred filtrate which turned colorless upon formation of a yellow precipitate. The precipitate was collected by filtration and dissolved in 100 mL of acetonitrile to give an orange solution. Several drops of water and ca. 1 mL of $SOBr_2$ were added to the stirred solution, which underwent an immediate color change to red. The solution was reduced to dryness leaving a red solid which was recrystallized by evaporation from a ca. 1:1 (v:v) mixture of acetone and toluene. The resulting red plates were washed with successive 30 mL aliquots of toluene, water, toluene and pentane, and dried under vacuum to afford 2.44 g (71%) of pure product. Absorption spectrum (MeCN): $\lambda_{max}$ ($\epsilon_M$) 395 (sh, 2380), 492 (781), 541 (1270) nm.

Anal. Calcd. for $C_{48}H_{109}Br_6N_3S_8Re_6$: C, 22.33; H, 4.26; Br, 18.57; N, 1.63; Re, 43.28; S, 9.94. Found: C, 22.37; H, 4.31; Br, 18.88; N, 1.58; Re, 43.16; S, 9.79.

$(Bu_4N)_4[Re_6S_8I_6].H_2O$.

A 1.12 g portion of the product recovered from a reaction targeting $Cs_6Re_6S_8I_8$ (as described above) was pulverized and stirred in 200 mL of 1M aqueous HI for 2 h. The mixture was filtered to give a large amount of gray-black solid and a yellow filtrate. Solid KOH (30 g, 0.53 mol) was added to the filtrate and stirred until it completely dissolved. A 50-mL aliquot of 0.05M aqueous $(Bu_4N)I$ was added to the stirred solution, which turned colorless upon formation of a yellow-orange precipitate. The precipitate was collected by filtration and dissolved in 100 mL of acetonitrile to give a yellow-orange solution. The solution was reduced to dryness leaving a yellow-orange solid that was crystallized by evaporation from a ca. 1:1 (v/v) mixture of acetone and toluene. The resulting yellow-orange plates were washed with successive 30 mL aliquots of toluene, water, toluene and pentane to afford 0.041 g (3.8%) of product. Absorption spectrum (MeCN): $\lambda_{max}$ ($\epsilon_M$) 393 (sh, 3290), 420 (2200), 507 (sh, 755) nm.

$(Bu_4N)_3[Re_6S_7(SH)I_6].2Me_2CO$.

The product recovered (2.69 g) from a reaction targeting $Cs_6Re_6S_8I_8$ (as described above) was pulverized and stirred in 200 mL of 1M aqueous $H_2SO_4$ for 1 h. The mixture was filtered to give a large amount of gray-black solid and a yellow-orange filtrate. A 50 mL aliquot of 0.05M aqueous $(Bu_4N)I$ was added to the stirred filtrate which turned colorless upon formation of a brown precipitate. The precipitate was collected by filtration and dissolved in 100 mL of $CH_2Cl_2$ to give a red-brown solution. Three drops of concentrated aqueous $H_2SO_4$ were added, and the solution was stirred for 30 min. The solution was then reduced to dryness, leaving a red solid which was recrystallized by evaporation from a ca. 1:1 (v/v) mixture of acetone and toluene. The resulting black crystals were washed with successive 30 mL aliquots of toluene, water, toluene and pentane to afford 0.22 g (9%) of product. Absorption spectrum (MeCN): $\lambda_{max}$ ($\epsilon_M$) 534 (590), 586 (sh, 353) nm.

$(Bu_4N)_3[Re_6Se_7(SeH)I_6].2Me_2CO$.

The product recovered (1.957 g) from a reaction targeting $Cs_4Re_6Se_8I_6$ (as described above) was pulverized and stirred in 200 mL of 1M aqueous HI for 2 h. The mixture was filtered to give a small amount of brown-black solid and a bright red filtrate. A 50 mL aliquot of 0.05M aqueous $(Bu_4N)I$ was added to the stirred filtrate which turned colorless upon formation of a brown precipitate. The precipitate was collected by filtration and dissolved in 100 mL of acetonitrile to give a red-brown solution. Ten drops of $SOCl_2$ were added, and the solution was stirred for 15 min. The solution was then reduced to dryness, leaving a brown-black solid which was crystallized by evaporation from a ca. 1:1 (v/v) mixture of acetone and toluene. The resulting black, block-shaped crystals were washed with successive 30 mL aliquots of toluene, water, toluene and pentane to afford 1.31 g (63%) of product. Absorption spectrum (MeCN): $\lambda_{max}$ ($\epsilon_M$) 477 (sh, 2060), 525 (sh, 1180), 609 (1190) nm.

Anal. Calcd. for $C_{48}H_{109}I_6N_3Se_8Re_6$: C, 17.72; H, 3.38; I, 23.43; N, 1.29; Re, 34.51; Se, 19.67. Found: C, 17.96; H, 3.42; I, 23.60; N, 1.26; Re, 34.32; Se, 19.36.

EXAMPLE 2

The $(BU_4N)_3[Re_6Se_7(SeH)I_6]$ compound prepared as above is converted to a range of phosphine-substituted analogues as shown in FIG. 1 hereinafter. More detailed structures of the compounds so produced are shown in FIG. 2 hereinafter.

EXAMPLE 3

A compound produced according to Example 2 may be converted to its dimer as shown in FIG. 3 hereinafter.

EXAMPLE 3

The $Cs_4[Re_6Se_8I_6]$ compound prepared as above is subjected to terminal ligand substitution as shown in FIGS. 4a and 4b hereinafter to yield the corresponding hexa(1,3,5-triaza-7-phospha-adamantanyl) compound. The 1,3,5-triaza-7-phospha-adamantane starting material is prepared according to Daigle, D. J. and Pepperman, A. B., J. Heterocyclic Chem ., 1975, 12, 579.

EXAMPLE 4

The $[Re_6Se_7(SeH)I_6]^{3-}$ compound prepared as above is subjected to terminal ligand substitution by MeCN as shown in FIGS. 5a and 5b hereinafter.

We claim:
1. A compound of formula (I)

$[M_6Q_8B_nL_{6-n}]^x$ where M is Re or Rh;
each Q is a bridging atom selected from O, S, Se and Te;
B is a monovalent non-bridging atom or moiety;
L is a $PR_3$ group in which R is $C_{1-6}$ alkyl or aryl, optionally substituted on the alkyl or aryl roup by one of more water-solubilising groups such as an amine or hydroxidy group, or the three R groups together form a $C_{6-10}$ trivalent group which may also contain up to three nitrogen or oxygen atoms;
n is an integer from 0 to 6;
and x is an integer from −2 to +4, representing the overall charge of the cluster, which when non-zero is accompanied by one or more counter ions of equal and balancing charge with the proviso that where M is $Re_3$, Q is $Te_3$, n=6, and x=+2, then B cannot be $TeBr_2$.

2. A compound according to claim 1 wherein B is a nitrile, an isonitrile, an amide, a halogen or a pseudohalogen.

3. A compound according to claim 2 wherein B is MeCN, MeNC, dimethyl formamide, Cl, Br, SCN or I.

4. A compound according to claim 1 wherein L is a triethylphosphine or triaza-phospha-adamantane group.

5. A dimer compound comprising two monomeric compounds, wherein each monomeric compound is a compound according to claim 1.

6. A diagnostic imaging contrast medium comprising a compound of formula (I) according to claim 1 complexed with one or more ligand molecules.

7. A diagnostic imaging contrast medium comprising a compound of formula (I) according to claim 1 complexed with one or more ligand molecules, together with at least one sterile pharmaceutical carrier or excipient.

8. A method of generating an image of a human or non-human animal body which method comprises administering to said body a physiologically tolerable contrast enhancing amount of a compound of formula (I) according to claim 1 complexed with one or more ligand molecules, and generating an image of at least said part of said body.

9. A method according to claim 8 in which said image is an X-ray image.

* * * * *